United States Patent
Lindenthaler

(10) Patent No.: US 9,409,014 B2
(45) Date of Patent: *Aug. 9, 2016

(54) METHOD FOR MODIFYING LARYNX POSITION BY TRANS-POSITIONING MUSCLE AND ELECTRODE STIMULATION

(71) Applicant: MED-EL Elektromedizinische Geraete GmbH, Innsbruck (AT)

(72) Inventor: Werner Lindenthaler, Oberperfuss (AT)

(73) Assignee: MED-EL Elektromedizinische Geraete GmbH, Innsbruck (AT)

( * ) Notice: Subject to any disclaimer, the term of this patent is extended or adjusted under 35 U.S.C. 154(b) by 0 days.

This patent is subject to a terminal disclaimer.

(21) Appl. No.: 14/819,512

(22) Filed: Aug. 6, 2015

(65) Prior Publication Data

US 2016/0030738 A1 Feb. 4, 2016

Related U.S. Application Data

(63) Continuation-in-part of application No. 14/289,935, filed on May 29, 2014, now Pat. No. 9,108,054.

(60) Provisional application No. 61/834,403, filed on Jun. 12, 2013.

(51) Int. Cl.
*A61N 1/36* (2006.01)
*A61N 1/05* (2006.01)
*A61B 17/24* (2006.01)

(52) U.S. Cl.
CPC ............ *A61N 1/36003* (2013.01); *A61B 17/24* (2013.01); *A61N 1/0551* (2013.01); *A61N 1/3601* (2013.01)

(58) Field of Classification Search
CPC ............ A61N 1/36003; A61N 1/0551; A61N 1/3601; A61B 17/32; A61B 17/24
See application file for complete search history.

(56) References Cited

U.S. PATENT DOCUMENTS

| | | | |
|---|---|---|---|
| 4,280,503 A | 7/1981 | Ackerman | |
| 4,488,561 A | 12/1984 | Doring | |

(Continued)

FOREIGN PATENT DOCUMENTS

| | | | |
|---|---|---|---|
| CA | 2414898 A1 | 9/2002 | |
| DE | 4228351 C1 | 4/1994 | |

(Continued)

OTHER PUBLICATIONS

Schuenke et al., "Atlas of Anatomy: Neck and Internal Organs," Ed. Lawrence Ross., New York, NY, Thieme, 2006, pp. 28 & 30.

(Continued)

*Primary Examiner* — Mark W Bockelman
(74) *Attorney, Agent, or Firm* — Sunstein Kann Murphy & Timbers LLP

(57) ABSTRACT

A method of modifying larynx position in a horse includes cutting one end of digastric muscle, attaching the cut end of the digastric muscle to thyroid cartilage or thyrohoid bone thereby trans-positioning the digastric muscle, providing a stimulation electrode configured to stimulate the trans-positioned digastric muscle, generating at least one stimulation parameter for the stimulation electrode using a processor, and stimulating the trans-positioned digastric muscle with the stimulation electrode using the stimulation parameter in order to modify the larynx position.

8 Claims, 22 Drawing Sheets

(56) References Cited

U.S. PATENT DOCUMENTS

| | | | |
|---|---|---|---|
| 5,111,814 | A | 5/1992 | Goldfarb |
| 5,269,769 | A | 12/1993 | Dhara et al. |
| 5,423,314 | A | 6/1995 | Schmid |
| 5,443,493 | A | 8/1995 | Byers et al. |
| 5,897,579 | A | 4/1999 | Sanders |
| 5,922,015 | A | 7/1999 | Schaldach |
| 6,078,841 | A | 6/2000 | Kuzma |
| 6,322,548 | B1 | 11/2001 | Payne et al. |
| 6,973,346 | B2 | 12/2005 | Hafer et al. |
| 6,978,787 | B1 | 12/2005 | Broniatowski |
| 7,917,220 | B2 | 3/2011 | Muller et al. |
| 8,136,532 | B2 | 3/2012 | Lindenthaler et al. |
| 8,380,313 | B2 | 2/2013 | Muller et al. |
| 8,430,860 | B2 | 4/2013 | Lindenthaler et al. |
| 8,460,270 | B2 | 6/2013 | Muller et al. |
| 8,788,036 | B2 | 7/2014 | Lindenthaler |
| 9,108,054 | B2 | 8/2015 | Lindenthaler |
| 2003/0045892 | A1 | 3/2003 | Kaladelfos |
| 2003/0120195 | A1 | 6/2003 | Milo et al. |
| 2005/0159743 | A1 | 7/2005 | Edwards et al. |
| 2006/0254595 | A1 | 11/2006 | Rea |
| 2006/0282127 | A1 | 12/2006 | Zealear |
| 2007/0078503 | A1 | 4/2007 | Kuzma et al. |
| 2007/0123950 | A1 | 5/2007 | Ludlow et al. |
| 2007/0156041 | A1 | 7/2007 | Rea |
| 2008/0071230 | A1 | 3/2008 | Lindenthaler |

FOREIGN PATENT DOCUMENTS

| | | |
|---|---|---|
| DE | 202005017959 U1 | 3/2006 |
| WO | 8808726 A1 | 11/1988 |
| WO | 9635469 A1 | 11/1996 |
| WO | 9728746 A1 | 8/1997 |
| WO | 0071063 A1 | 11/2000 |
| WO | 0158516 A1 | 8/2001 |
| WO | 03070133 A1 | 8/2003 |
| WO | 2007057127 A1 | 5/2007 |

OTHER PUBLICATIONS

International Searching Authority, International Search Report-International Application No. PCT/US2007/077296 dated Feb. 26, 2008, together with the Written Opinion of the International Searching Authority, 15 pages.

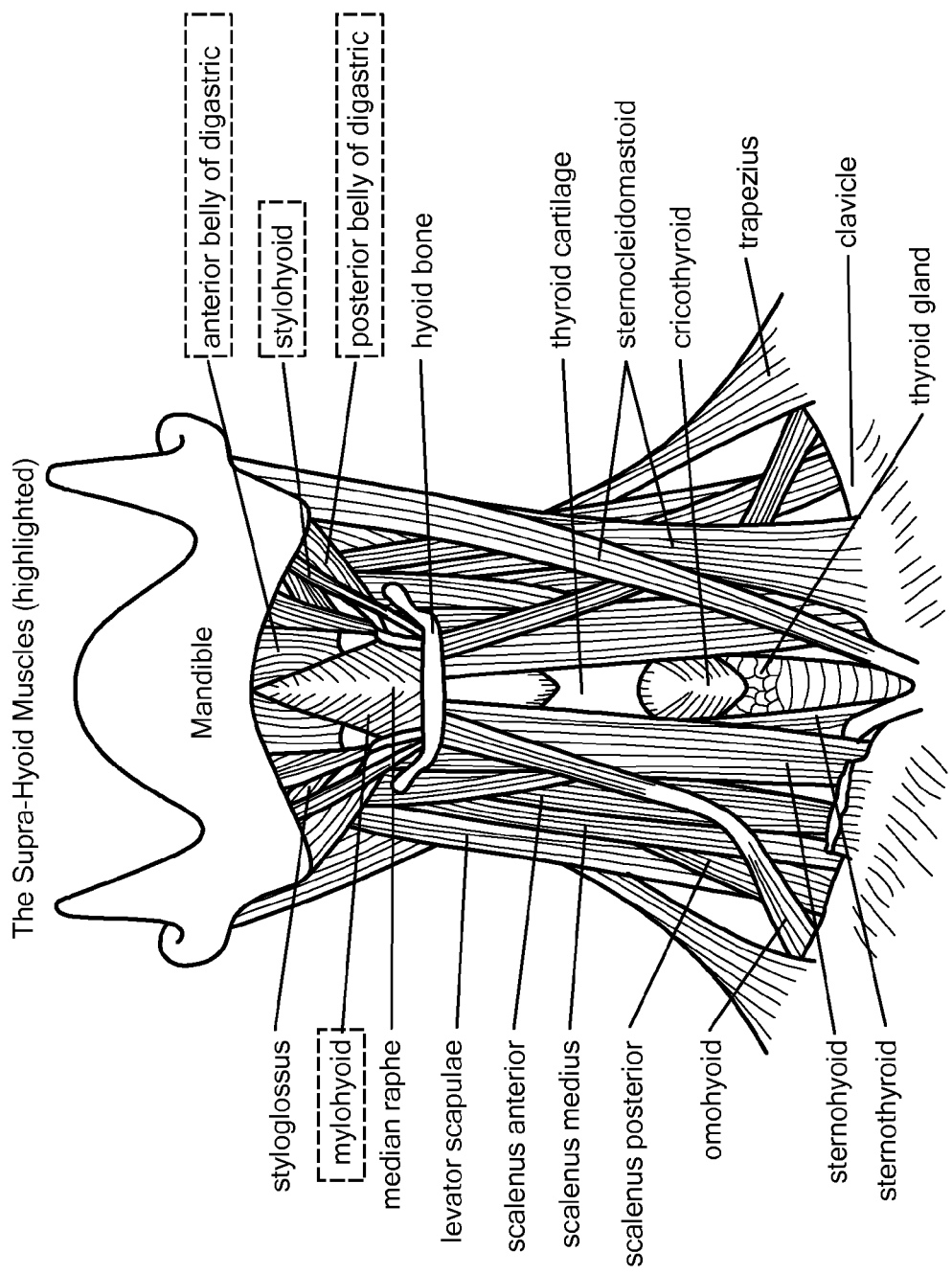

METHOD FOR MODIFYING LARYNX POSITION BY TRANS-POSITIONING MUSCLE AND ELECTRODE STIMULATION

CROSS REFERENCE TO RELATED APPLICATIONS

This patent application is a continuation-in-part of U.S. patent application Ser. No. 14/289,935 filed May 29, 2014, which claims the benefit of U.S. Provisional Patent Application No. 61/834,403 filed Jun. 12, 2013, the disclosures of which are incorporated by reference herein in their entirety.

TECHNICAL FIELD

The present invention relates generally to control of muscular activity by electrode stimulation, and in particular, to devices and methods for modifying the position of the larynx in order to ensure open airways.

BACKGROUND ART

Respiratory problems in horses may affect the upper or lower airways. The upper airways include the nostrils, the nasal passages, the guttural pouch and the larynx. The larynx is the junction between the nasal cavity and the trachea, and coordinates swallowing and protects the trachea and thus the lungs from the inhalation of food. The arytenoid cartilages, which are located in front of the trachea, are triangular-shaped, paired structures that are pulled open during inspiration to allow for an unobstructed airflow into the trachea. The larynx is innervated by the recurrent laryngeal nerves (RLN) which contain motor fibers that innervate both the abductor/opener and adductor/closer muscles of the arytenoid cartilages and their associated vocal folds. The larynx moves position when the horse swallows due to its attachments to the tongue and the basihyoid bone of the hyoid apparatus by the thyrohyoid membrane. The upper airway structures in a horse, and in particular the larynx, are susceptible to various disorders which affect the horse's health and its ability to perform normally since horses can only breathe through their nose.

Three common upper airway disorders affecting horses are left laryngeal hemiplegia, intermittent dorsal displacement of the soft palate, and epiglottic entrapment. In these disorders, normal airflow is compromised due to the collapse of tissue into the airway resulting in partial airway obstruction. For example, laryngeal hemiplegia is a distal axonopathy affecting the left RLN causing a unilateral disease. Damage to the left RLN compromises both the abductor and adductor functions by stopping vocal fold movement in a position just lateral to the midline. One surgical treatment for laryngeal hemiplegia is prosthetic laryngoplasty. In this treatment, the paralyzed left arytenoid cartilage is sutured in an open position to restore airflow. Conventional methods of treatment have been useful in some horses, but the treatments are clearly less than ideal since they have modest success rates, significant complications, and do not slow the progression of the disease. Thus, the disease often reaches a state where these methods do not help anymore.

Electrical stimulation has been successfully used for controlling weakened muscles/nerves, such as aged or degenerated nerves/muscles, for controlling re-innervating nerves, including synkinetically re-innervating nerves, and/or for providing electrical signals to nerves in order to compensate for hearing deficiencies (e.g., cochlear implant stimulation for providing hearing sensations to deaf people) or to overrule wrong elicited nerve signals.

Various stimulation systems and methods have been proposed to control the upper respiratory muscles, but none of them addresses the elevation of the larynx in order to provide open airways in horses. For example, Freed et al. describe a non-invasive method and apparatus that continuously stimulates the skin surface to assist patients in initiating a swallow (see, e.g., U.S. Pat. Nos. 5,725,564, 6,104,958, and 5,891,185). In addition, there are systems which cause glottis closure by means of appropriate electrical stimulation (see, e.g., Bidus et al., Laryngoscope, 110:1943-1949, 2000; Ludlow et al., Journal of Artificial Organs, 23:463-465, 1999; and Ludlow et al., Muscle and Nerve, 23:44-57, 2000). In U.S. Pat. Appl. No. 2007/0123950, Ludlow et al. disclose a method and system for synergistic production of muscle movements during speech, swallowing or voice production by moving the hyoid bone and/or parts of the upper airway and/or vocal tract by means of electrical stimulation of at least two different muscles. Ludlow et al. found that neuromuscular stimulation of only two of the muscles yields a large proportion of normal desired movement for the hyoid bone. Further, Ludlow et al. disclose that the muscles involved in swallowing remain at their normal, given locations within a human's body. In U.S. Pat. Appl. No. 2008/0208280, Lindenthaler discloses a method and system for treating an airway disorder in a horse that involves stimulating the airway tissue.

SUMMARY OF EMBODIMENTS

In accordance with one embodiment of the invention, a method of modifying larynx position in a horse includes cutting one end of the tendons of digastric muscle, attaching the cut end of the tendon of the digastric muscle to thyroid cartilage or thyrohyoid bone, thereby trans-positioning the digastric muscle, providing a stimulation electrode configured to stimulate the trans-positioned digastric muscle, generating at least one stimulation parameter for the stimulation electrode using a processor, and stimulating the trans-positioned digastric muscle with the stimulation electrode using the stimulation parameter in order to modify the larynx position.

In accordance with another embodiment of the invention, a method of modifying larynx position in a human subject includes cutting one end of the tendons of digastric muscle, attaching the cut end of the tendon of the digastric muscle to thyroid cartilage, thereby trans-positioning the digastric muscle, providing a stimulation electrode configured to stimulate the trans-positioned digastric muscle, generating at least one stimulation parameter for the stimulation electrode using a processor, and stimulating the trans-positioned digastric muscle with the stimulation electrode using the stimulation parameter in order to modify the larynx position.

In related embodiments, the one cut end may be the posterior belly of the digastric muscle. The stimulation may be electrical stimulation of the digastric muscle, its innervating nerves, and/or a reflex of the digastric muscle, such as the anterior digastric muscle. The method may further include providing a sensing electrode configured to detect activity of a muscle involved in the swallowing process or the respiration process and to generate a first signal based on the detected activity. The at least one stimulation parameter may be generated in response to receiving the first signal, and the stimulation parameter may be based on the first signal. The sensing electrode may be configured to detect electromyographic (EMG) activity of the muscle involved in the swallowing or respiration process and/or may be configured to detect the physical movement activity of the muscle involved in the swallowing or respiration process. The stimulation may be manually activated by the subject and/or may be activated by the activity of the anterior belly of digastric muscle. The stimulating may modify the larynx position by moving the larynx towards the chin.

BRIEF DESCRIPTION OF THE DRAWINGS

The foregoing features of the invention will be more readily understood by reference to the following detailed description, taken with reference to the accompanying drawings, in which:

FIG. 1A is an anterior view of a neck of a human showing various muscles and associated structures;

DESCRIPTION OF ILLUSTRATIVE EMBODIMENTS

Figure 1B:
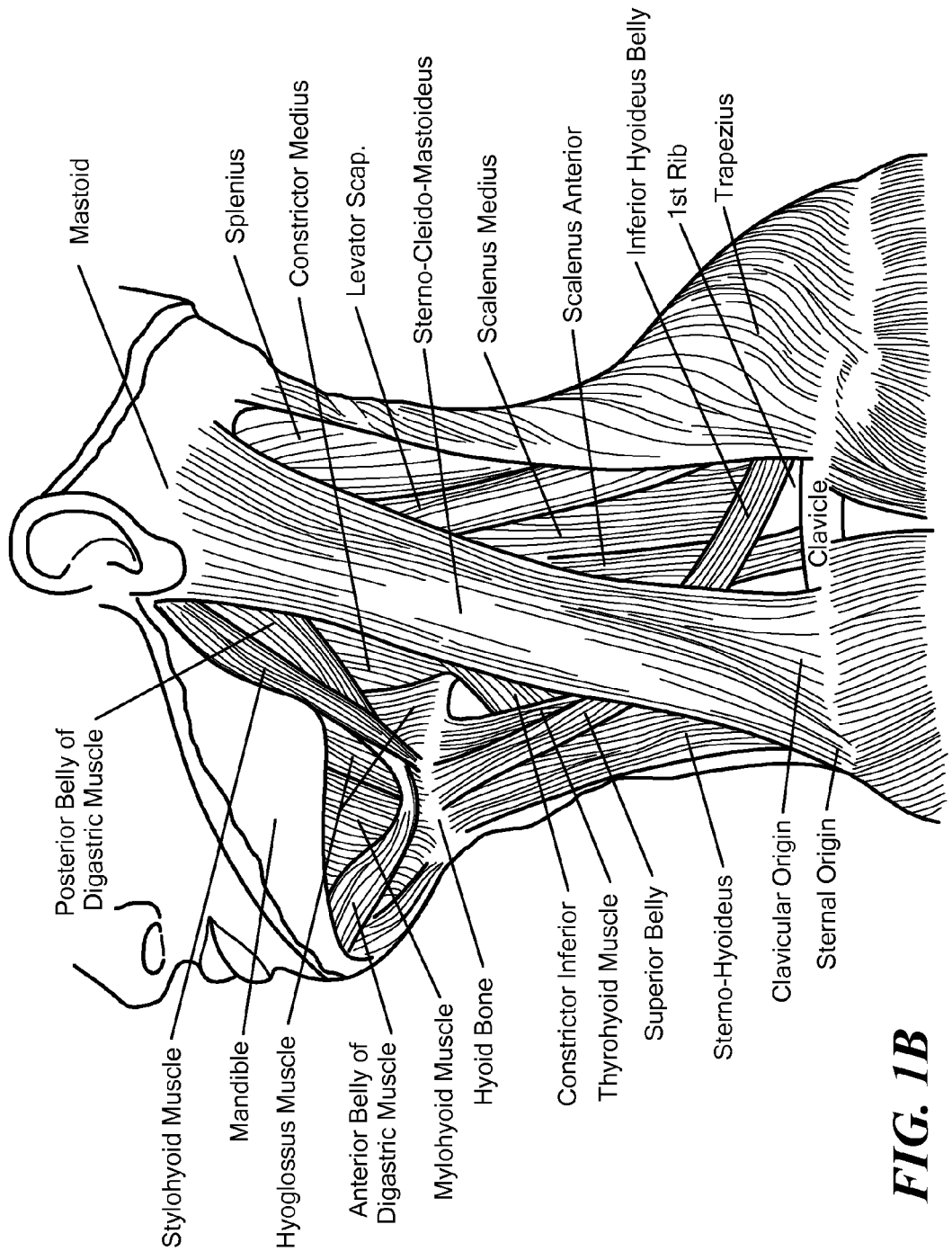
FIG. 1B is a lateral view of the neck muscles of a human.

Embodiments of the present invention provide a method of trans-positioning a neck muscle and its subsequent stimulation to cause a desired movement of the larynx to protect the airway in order to prevent aspiration in subjects suffering from dysphagia or horses suffering from disorders of the upper airway. Embodiments include a system and method for electrical stimulation of at least one trans-positioned muscle and/or electrical stimulation of an innervating nerve of at least one trans-positioned muscle. In particular, embodiments disclose electrically stimulating (directly or via innervating nerve) trans-positioned muscle tissue attached to the chin on one side and the thyroid cartilage or thyrohyoid bone at the other side. This may be more successful in elevating the larynx than electrode excitation of one or more muscle(s) attached to the center or near the center of a biaxial cartilage, tissue or bone (e.g., the hyoid bone or hyoid apparatus). The desired movement of the larynx should provide substantially pure elevation of the larynx or elevation of the larynx and movement towards the chin.

Although the figures and related description below show the posterior belly of the digastric muscle being cut and the anterior cut end being moved in the subject, virtually any submental, sub-thyroid or supra-thyroid muscle that is large enough to be trans-positioned between the chin and the thyroid cartilage or thyrohyoid bone may be used in embodiments of the present invention. Preferably, striated muscles that attach to ligaments and tendons which move bones, or to cartilage, may be used. It may be advantageous to use one muscle, a paired muscle, or more muscles engaged in the upper respiratory or swallowing systems. Generally, the most preferable muscles can be considered as one of three types, categorized as muscle groups that work together for three different physiological functions: swallowing, respiration and movement of the neck.

For example, one appropriate group of muscles that creates the swallowing motion in a human subject includes the mylohyoid, thyrohyoid, geniohyoid, hyoglossus, palatopharyngeus, cricopharyngeus, inferior constrictor, superior constrictor, anterior and posterior bellies of the digastric, genioglossus, temporalis, levator veli palatini, tensor veli palatini, palatoglossus, inferior longitudinal and superior longitudinal muscles of the tongue, styloglossus, thyroarytenoid, lateral cricoarytenoid, and interarytenoid muscles.

Another appropriate group of muscles are one, two paired or even more muscles, such as the bilateral mylohyoid muscle (s), the bilateral thyrohyoid muscle(s), the bilateral geniohyoid muscle, the unilateral mylohyoid muscle(s), the unilateral geniohyoid muscle(s), the unilateral thyrohyoid muscle(s), the geniohyoid and thyrohyoid muscle combination, the mylohyoid and thyrohyoid muscle combination, the geniohyoid and the mylohyoid muscle combination.

Another appropriate group of muscles are the sub-thyroid and supra-thyroid muscles. These pairs of muscles are attached to the thyroid cartilage by one of their ends. This group of muscles includes the thyrohyoid and sternothyroideus.

Additional muscles of interest may include the lateral pterygoid, medial pterygoid, anterior belly of the digastric, obicularis oris, buccinator, zygomaticus, depressor labi inferior, mentalis, levator labi superior, genioglossus, inferior longitudinal and superior longitudinal muscles of the tongue, styloglossus, temporalis, levator veli palatini, tensor veli palatini, palatoglossus, styloglossus, thyroarytenoid, lateral cricoarytenoid, posterior cricoarytenoid, cricothyroid, stylohyoid, interarytenoid muscles, and sternothyroid.

Intramuscular electrode(s) or electrodes next to or around these trans-positioned muscles or their respective innervating nerves in one or more combinations of these muscles/nerves in a subject may be used to affect a swallowing motion, to enhance swallowing motion, to initiate swallowing motion, to augment swallowing motion, and/or to produce or enhance part of a complex pattern of movement during swallowing. Intramuscular electrode(s) or electrodes next to or around these trans-positioned muscles or their respective innervating nerves in one or more combinations of these muscles/nerves in a horse may be used to ensure open airways. Details of illustrative embodiments are discussed below.

FIGS. 1A and 1B are anterior and lateral views, respectively, of a human's neck showing various muscles and associated structures in their natural positions. FIGS. 1A and 1B specifically show the anterior and posterior belly of the digastric muscle as well as the thyroid cartilage to which the trans-positioned muscle may be fixed, as described in more detail below.

Figure 2A:
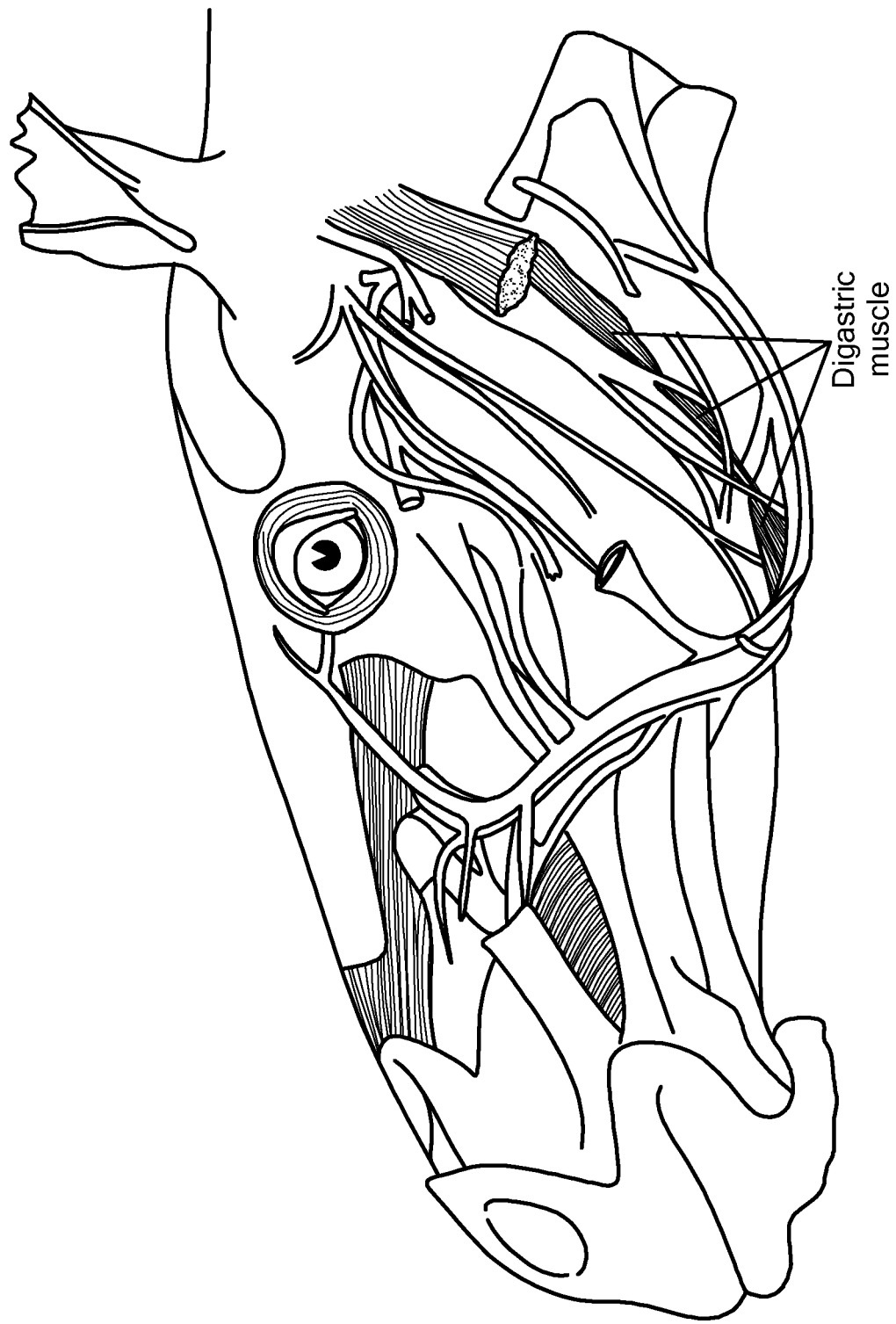
FIG. 2A is a lateral view of a neck of a horse showing the digastric muscle.
Figure 2B:
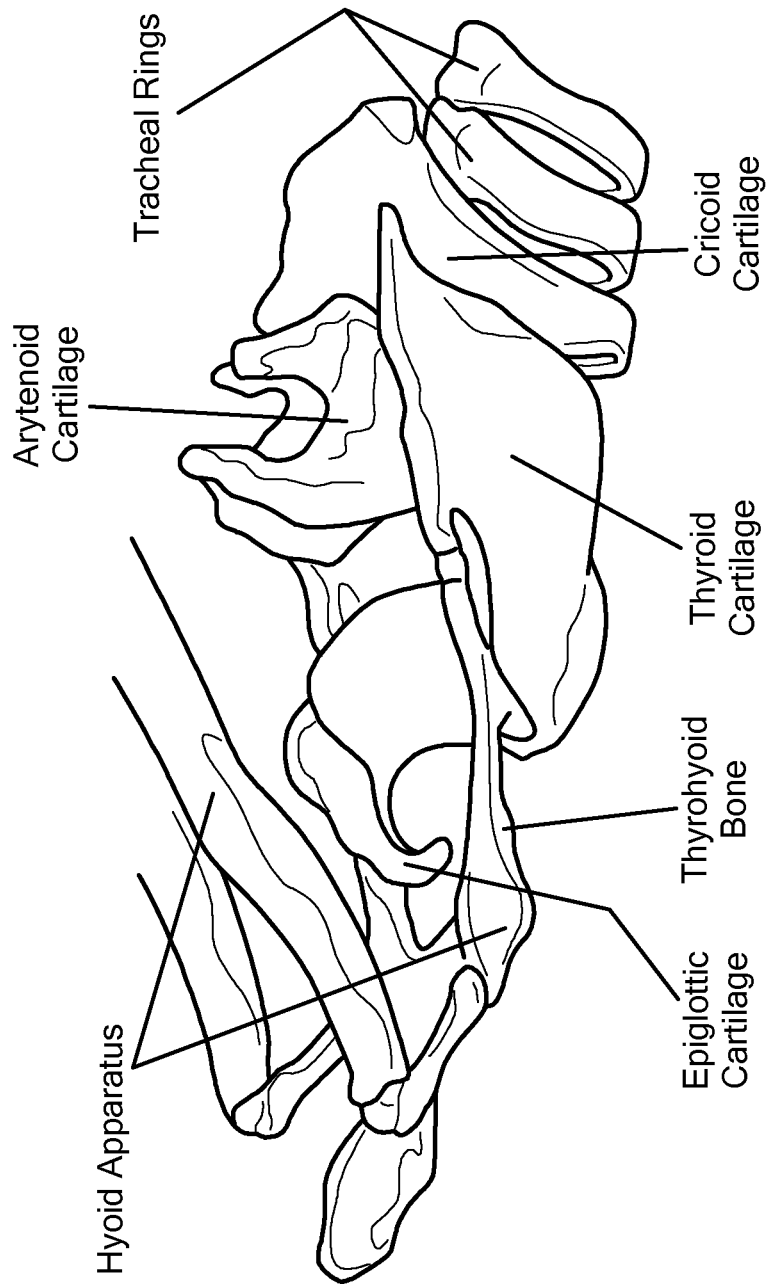
FIG. 2B shows a lateral view of various structures in the neck of a horse.

FIG. 2A is a lateral view of a horse's neck, and FIG. 2B is a lateral view of various structures in the horse's neck in their natural positions. FIGS. 2A and 2B show the digastric muscle as well as the thyroid cartilage or thyrohyoid bone to which the trans-positioned muscle may be fixed, as described in more detail below.

Figure 3:
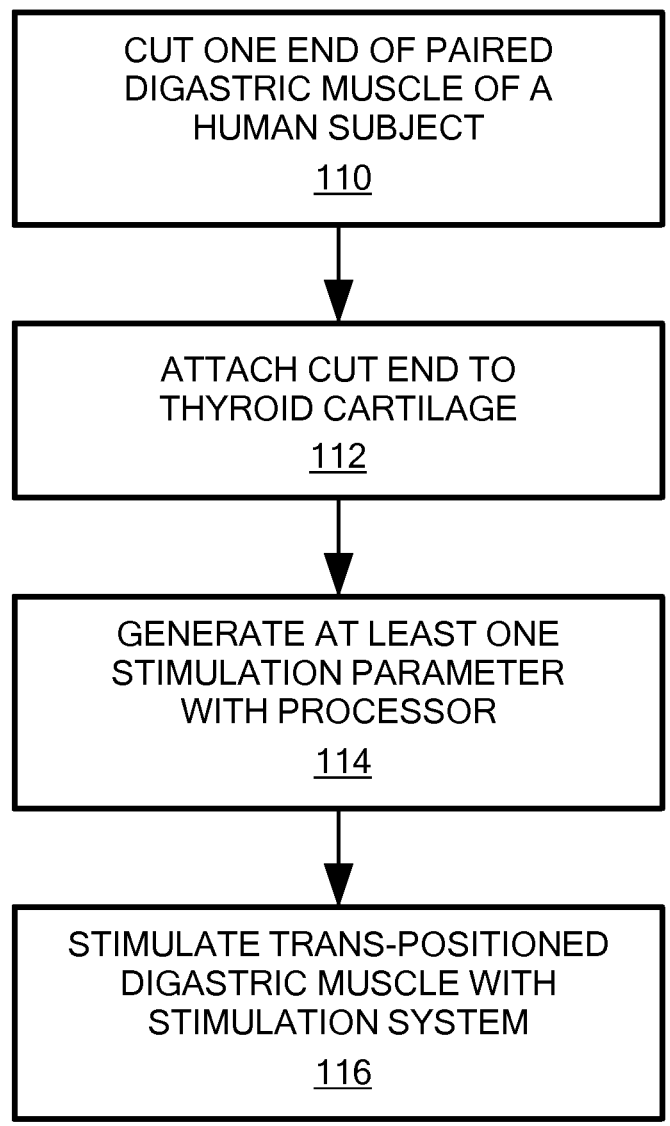
FIG. 3 is a flow chart illustrating a method for modifying larynx position in a human subject in accordance with an embodiment of the invention.
Figure 4A:
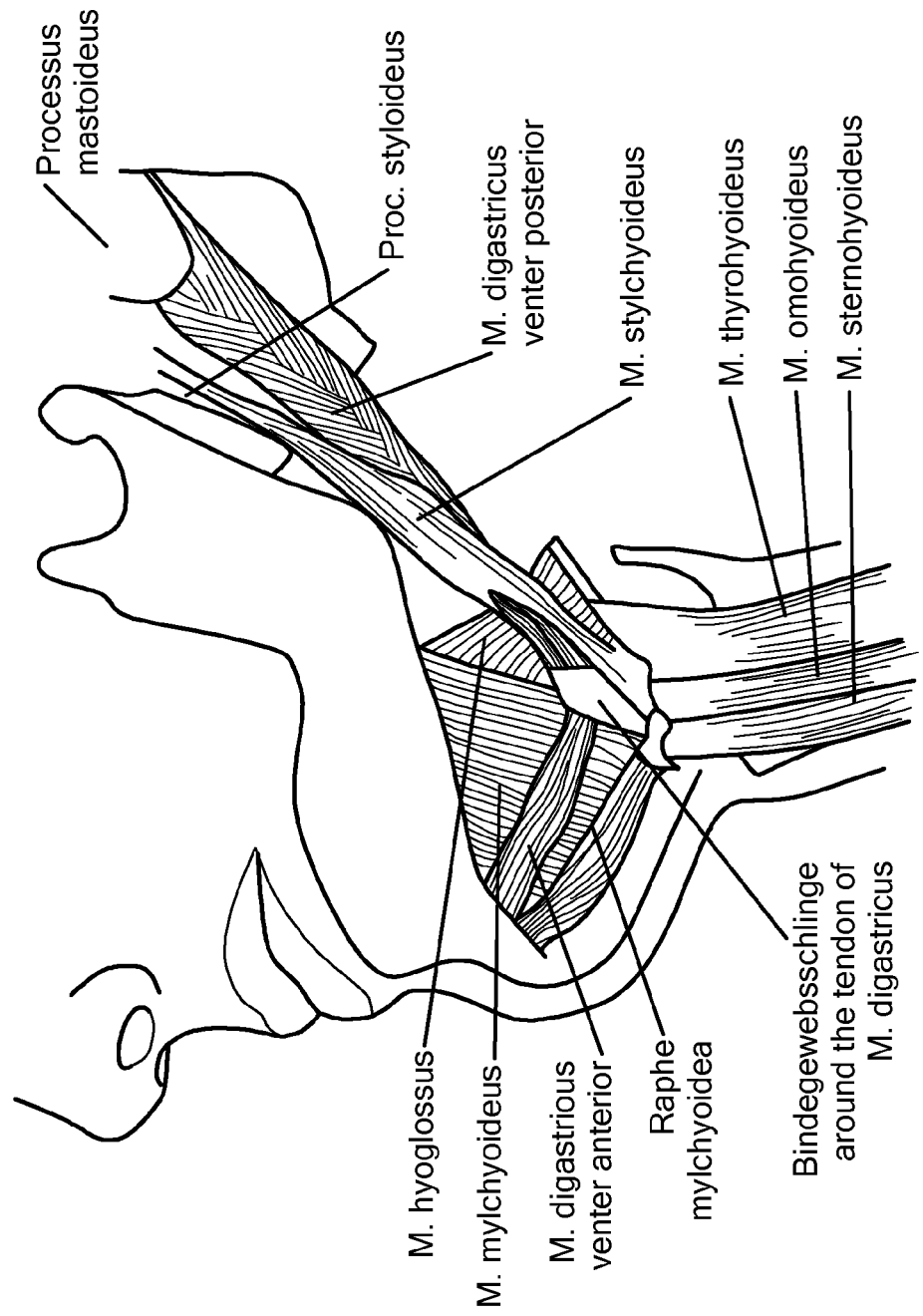
FIGS. 4A-4G show schematic illustrations of a method of trans-positioning a neck muscle in a subject in accordance with an embodiment of the invention.
Figure 4B:
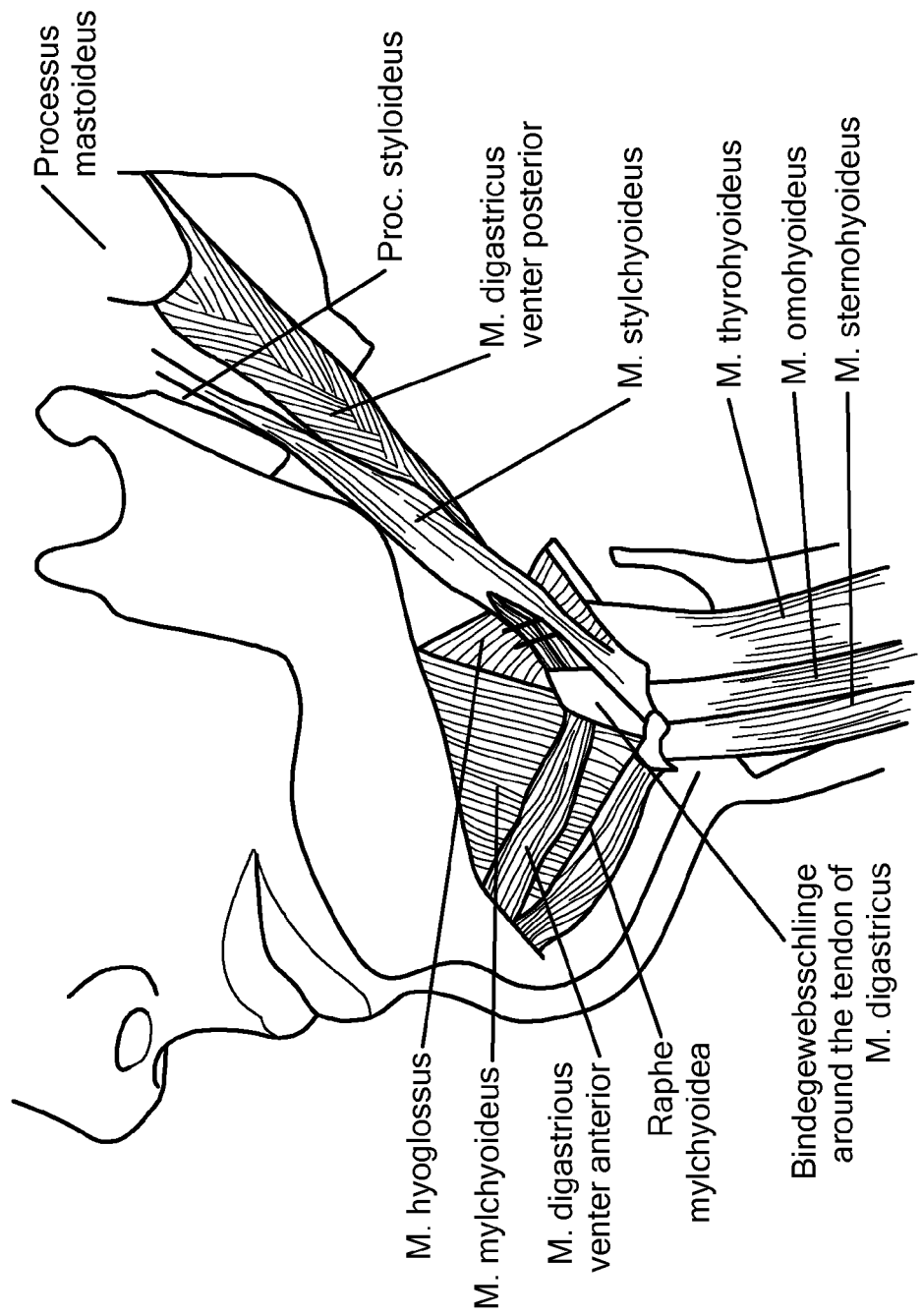
Figure 4C:
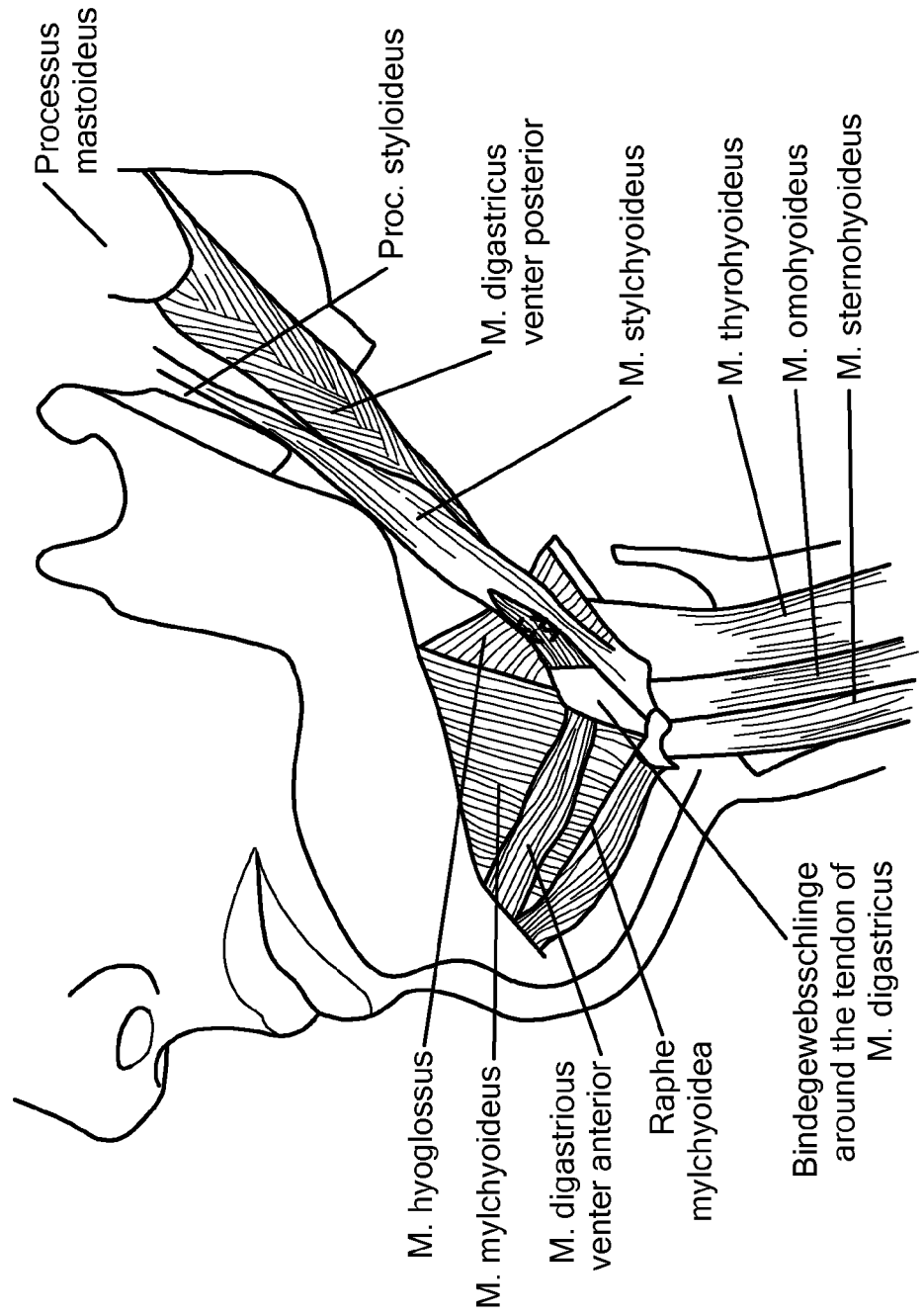

FIG. 3 shows a process 100 for modifying larynx position in a subject according to embodiments of the present invention. FIGS. 4A-4H schematically show various views of the neck muscles during the trans-positioning process discussed in FIG. 3. The process begins at step 110, in which one end of the paired digastric muscle is cut. FIG. 4A shows the neck muscles in their natural position, and FIGS. 4B and 4C show the location of the cut (straight lines) at the posterior belly of the paired digastric muscle and its separation location (arrows).

Figure 4D:
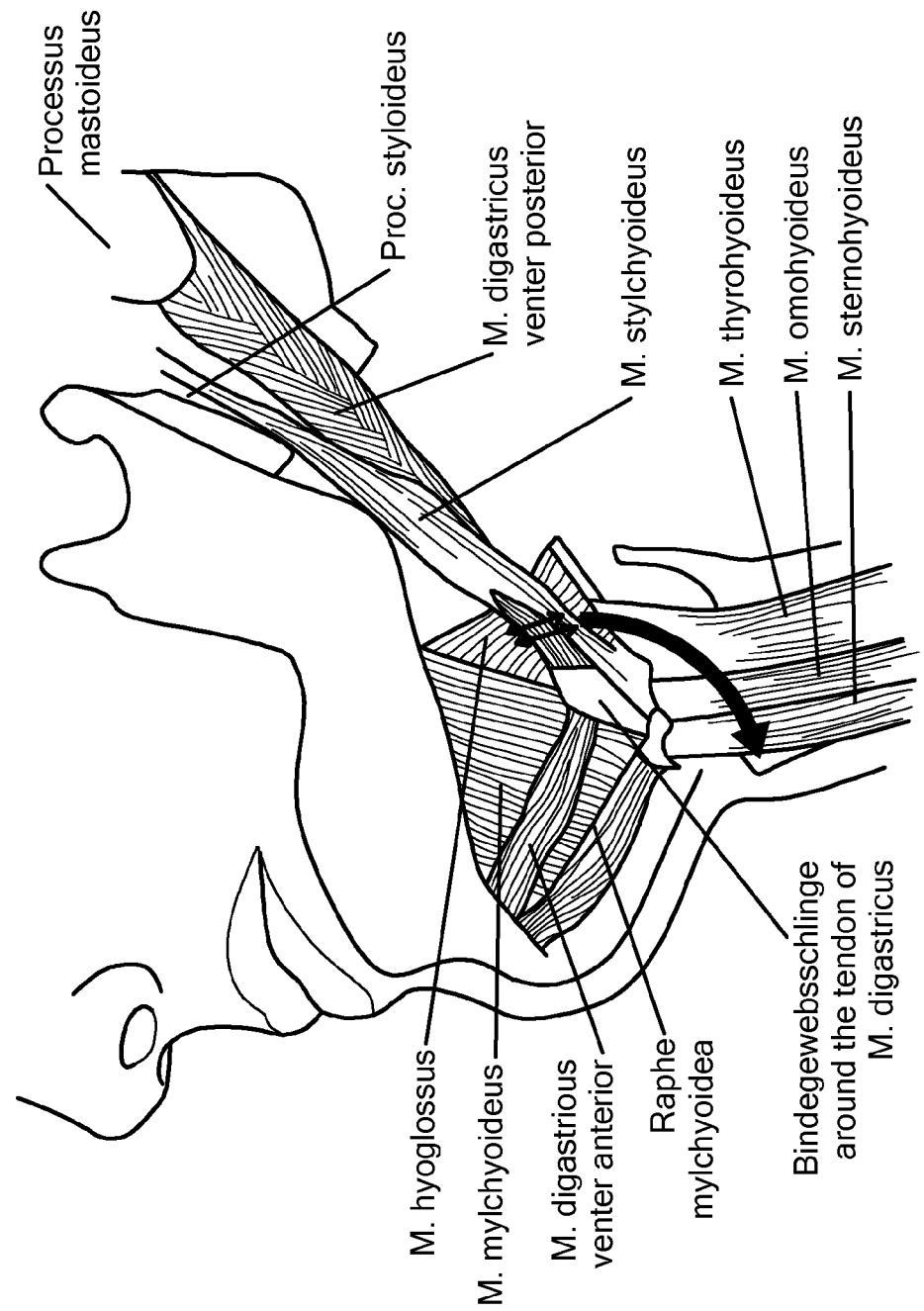
Figure 4E:
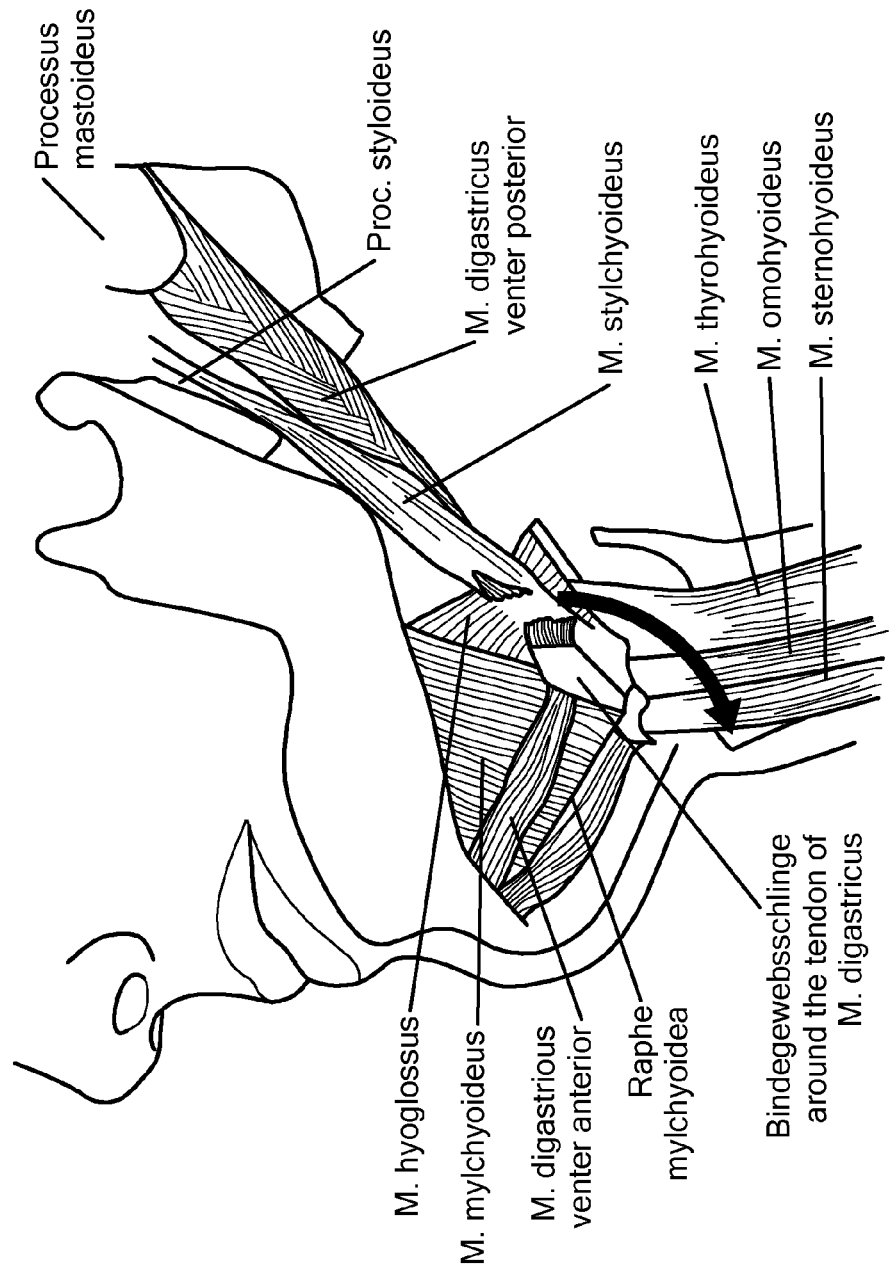
Figure 4F:
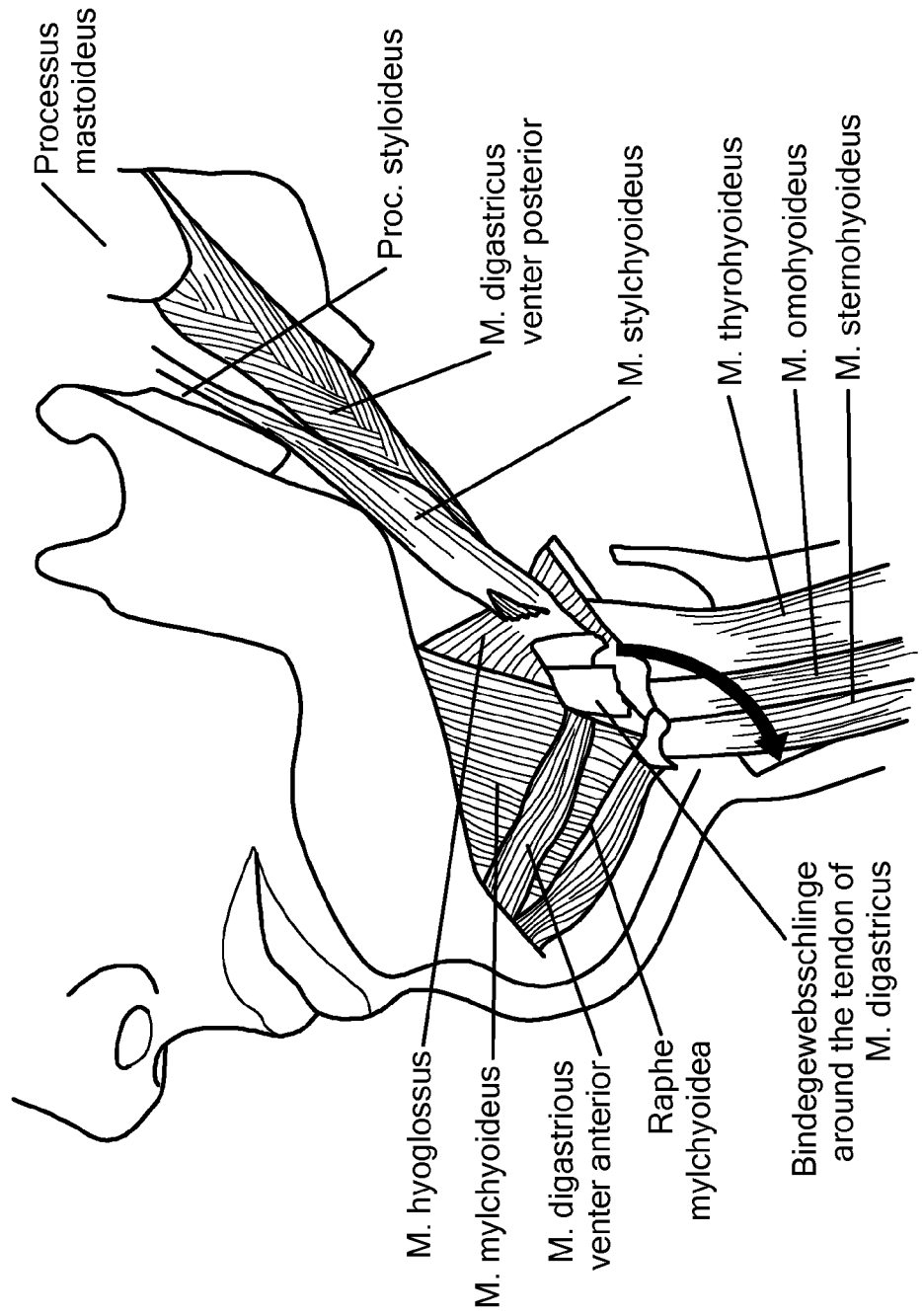
Figure 4G:
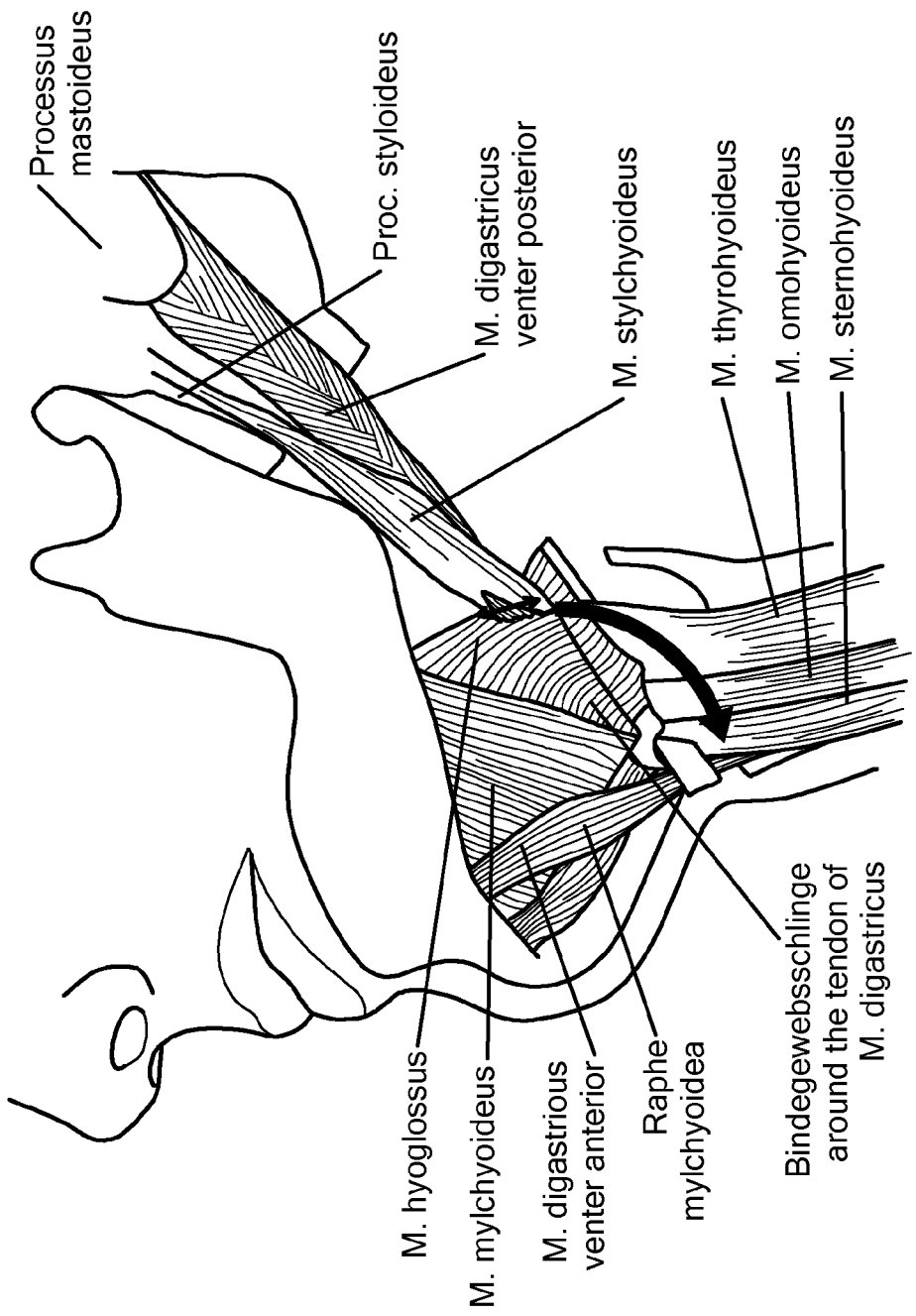
Figure 4H:
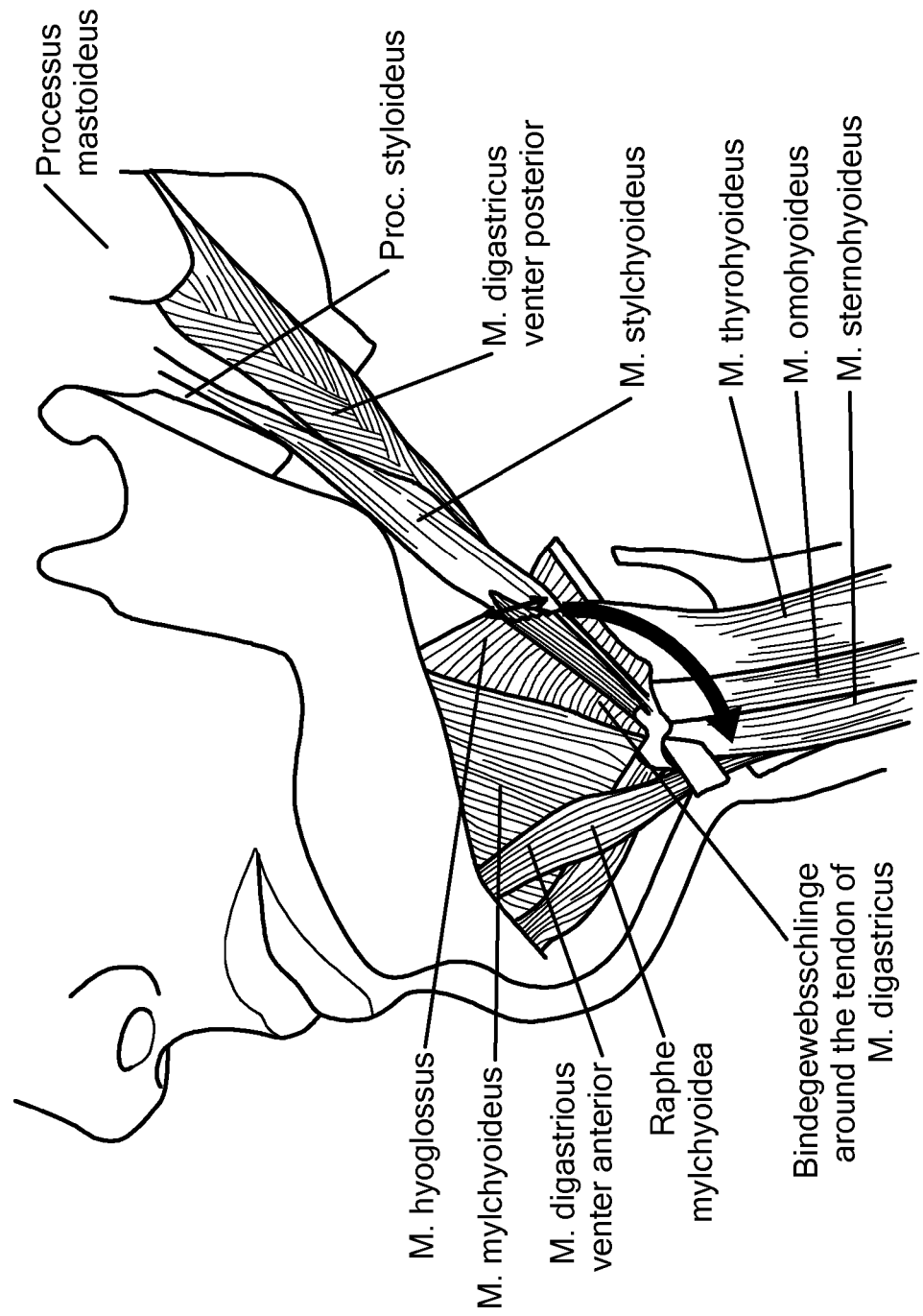
FIG. 4H shows a schematic illustration of an alternative method of trans-positioning a neck muscle in a subject in accordance with an embodiment of the invention.

In step 112, the cut end is attached to the thyroid cartilage. FIG. 4D shows the movement direction of the cut end (arrow), FIG. 4E shows the posterior belly of the paired digastric muscle cut, and 4F shows the severed ends of the paired digastric muscle and its attachment location (shown with an arrow). FIG. 4G shows the cut end attached to the thyroid cartilage. Although FIG. 4G shows the stylohyoid muscle also cut, the trans-positioning of the digastric muscle may be done without cutting or damaging the stylohyoid muscle, such as shown in FIG. 4H. The stylohyoid muscle lies anterior and superior to the posterior belly of the digastric muscle and functions to draw the hyoid bone backwards and elevate the tongue. The trans-positioned muscle(s) may be called geniothyroid muscle(s).

Figure 5B:
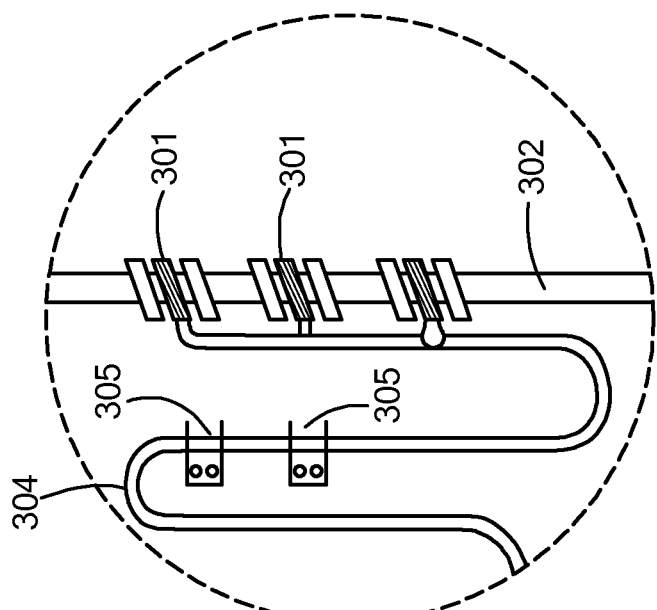
FIG. 5B is an exploded view of the circled region in FIG. 5A.
Figure 5A:
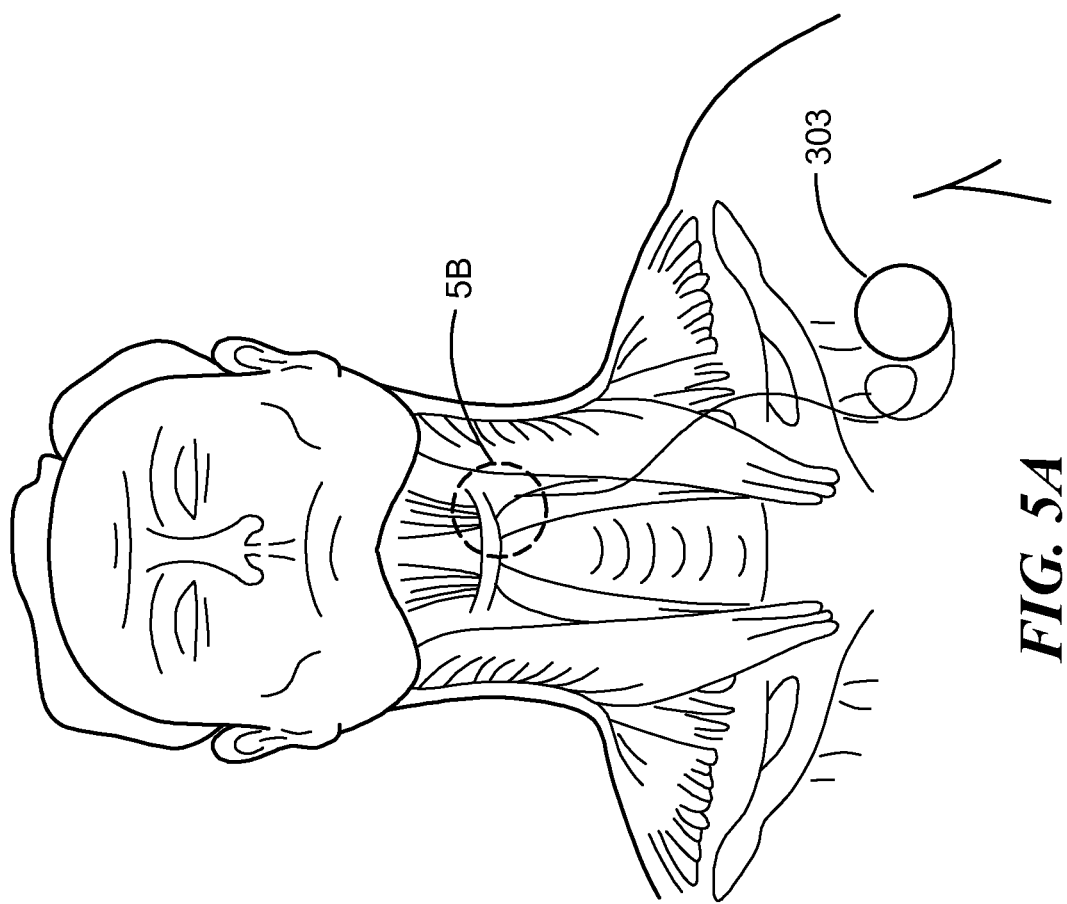
FIG. 5A shows a stimulation system used for modifying a larynx position in a subject in accordance with an embodiment of the invention.

In step 114, at least one stimulation parameter is generated with a processor. FIGS. 5A and 5B schematically show a stimulation system that may be used with embodiments of the present invention. The stimulation system may include a processor 303, which may include a pulse generator that generates a stimulation parameter. The processor 303 may be implanted in the patient's chest. In humans, the stimulation parameter may be a biphase current pulse, and the biphase current pulse may have a duration of about 0.001 ms to 50 ms, in most subjects from about 0.1 msec to 5 msec, and a magnitude in the range of about 0.05 mA to 20 mA, in most subjects from about 0.5 mA to 5 mA. Appropriate stimulation systems that may be used with embodiments of the present invention are disclosed in U.S. Pat. Nos. 9,026,204 by Lindenthaler, U.S. Pat. No. 8,731,683 by Lindenthaler, and U.S. Pat. No. 9,050,462 by Lindenthaler, incorporated by reference herein in their entirety.

In step 116, the trans-positioned digastric muscle is stimulated with the stimulation system in order to move the larynx position during the swallowing process. The trans-positioned muscle may be stimulated either by a muscle electrode, by stimulating its/their innervating nerve(s), or by a reflex of the anterior belly of the digastric muscle. For example, the stimulation system may include stimulating electrodes 301 that may be wrapped around or placed near or in contact with branches of the hypoglossus nerve 302, such as shown in FIGS. 5A and 5B. The stimulation system may include electrode leads 304 and optional safety loops 305, such as shown in FIG. 5B.

Figure 6:
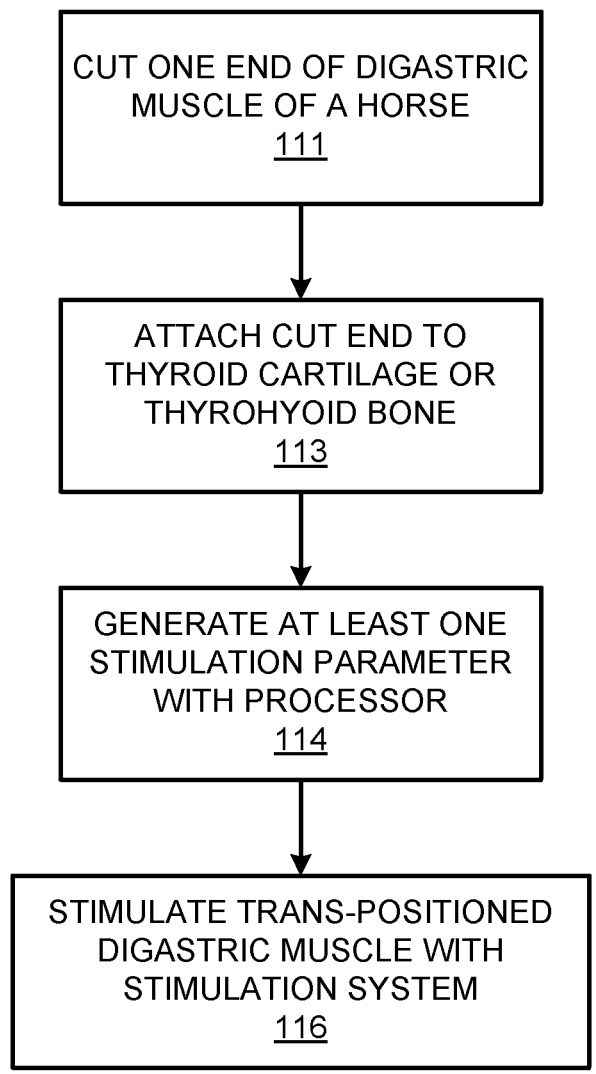
FIG. 6 is a flow chart illustrating a method for modifying larynx position in a horse in accordance with an embodiment of the invention.
Figure 7A:
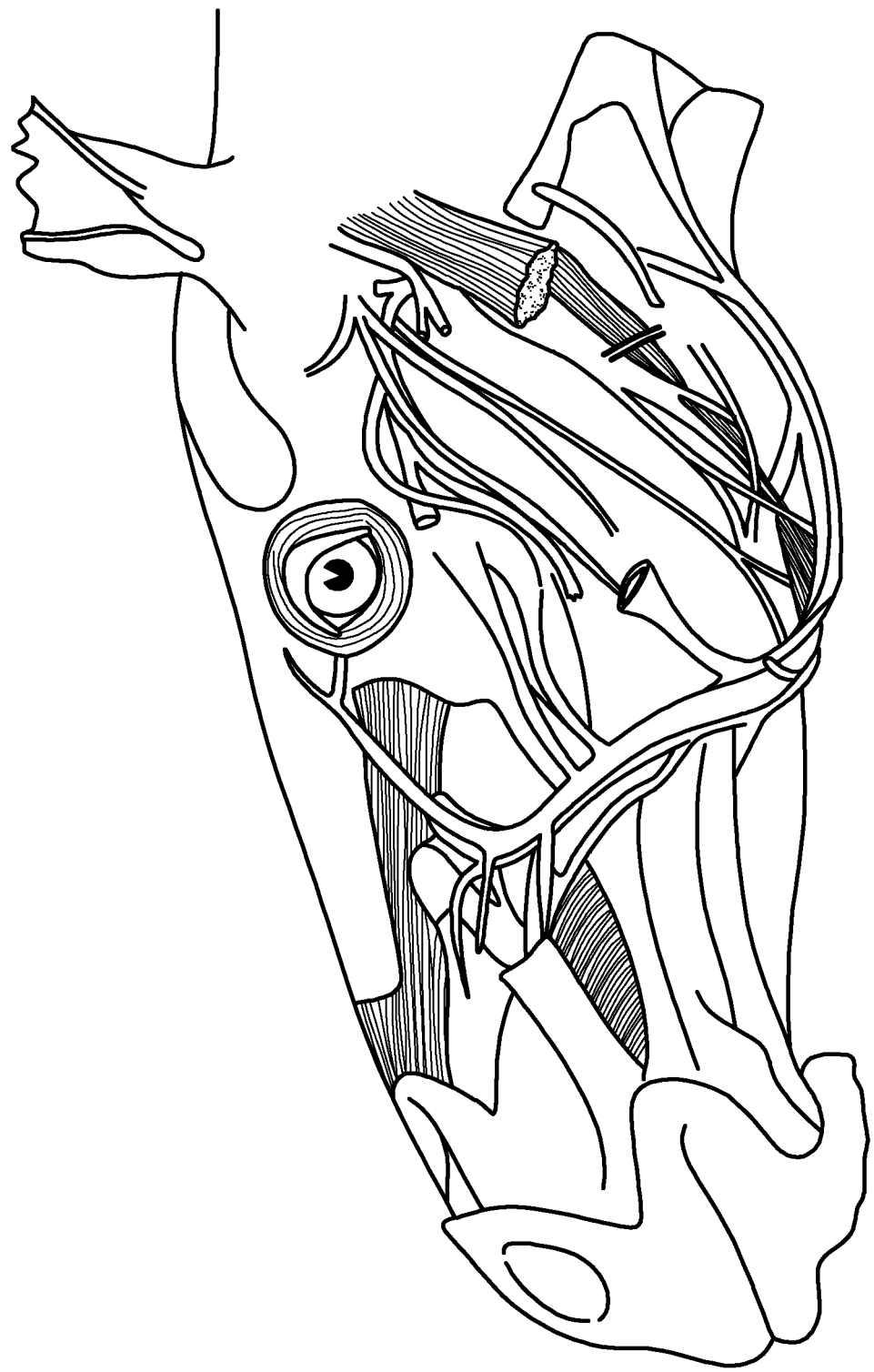
FIGS. 7A-7E show schematic illustrations of a method of trans-positioning a neck muscle in a horse in accordance with an embodiment of the invention.
Figure 7B:
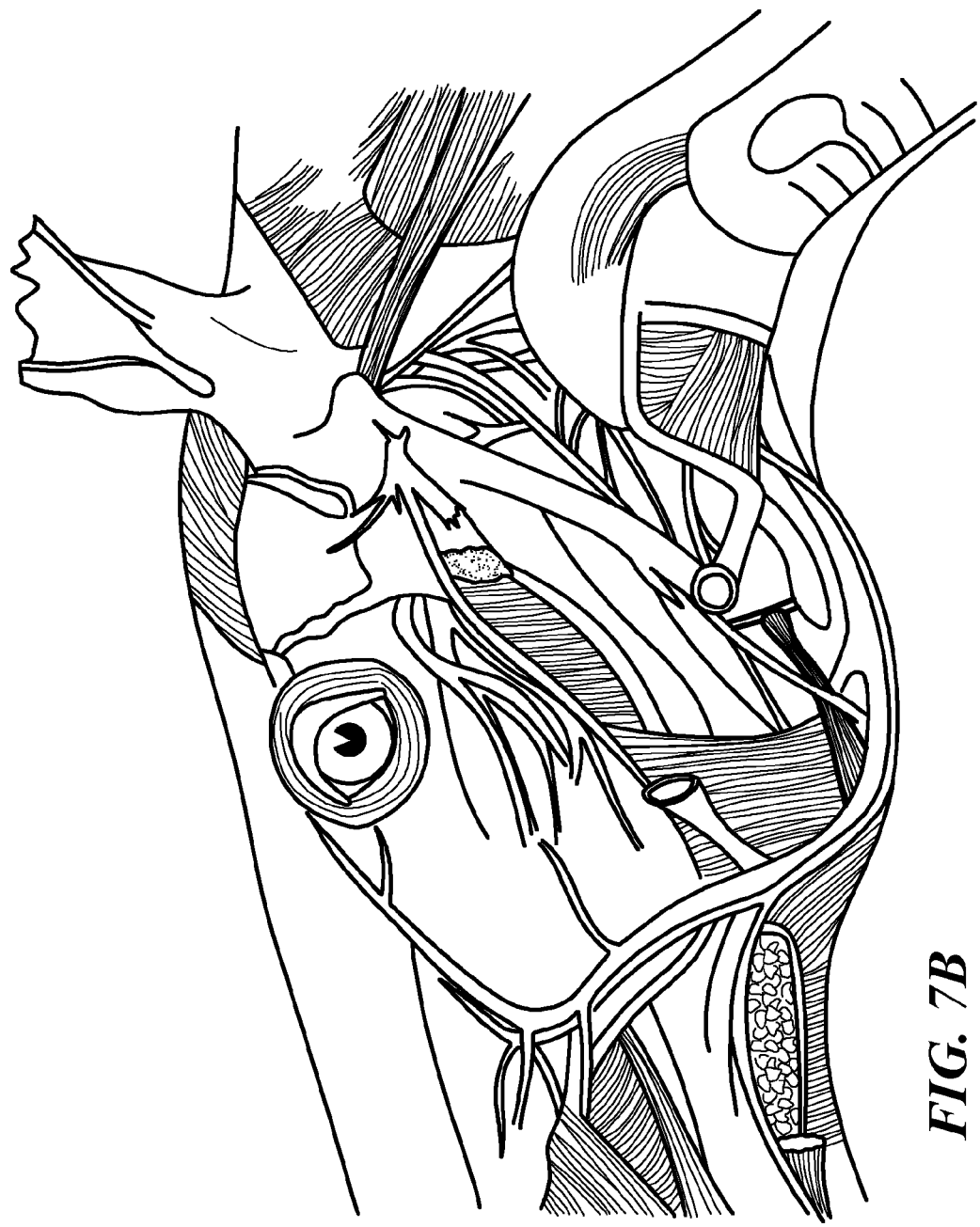

FIG. 6 shows a process 200 for modifying larynx position in a horse according to embodiments of the present invention. FIGS. 7A-7E schematically show various views of the neck muscles during the trans-positioning process discussed in FIG. 6. The process begins at step 111, in which one end of the digastric muscle is cut. FIG. 7A shows the neck muscles in their natural position with the location of the cut (black straight line) on the digastric muscle. FIG. 7B shows the digastic muscle cut.

Figure 7C:
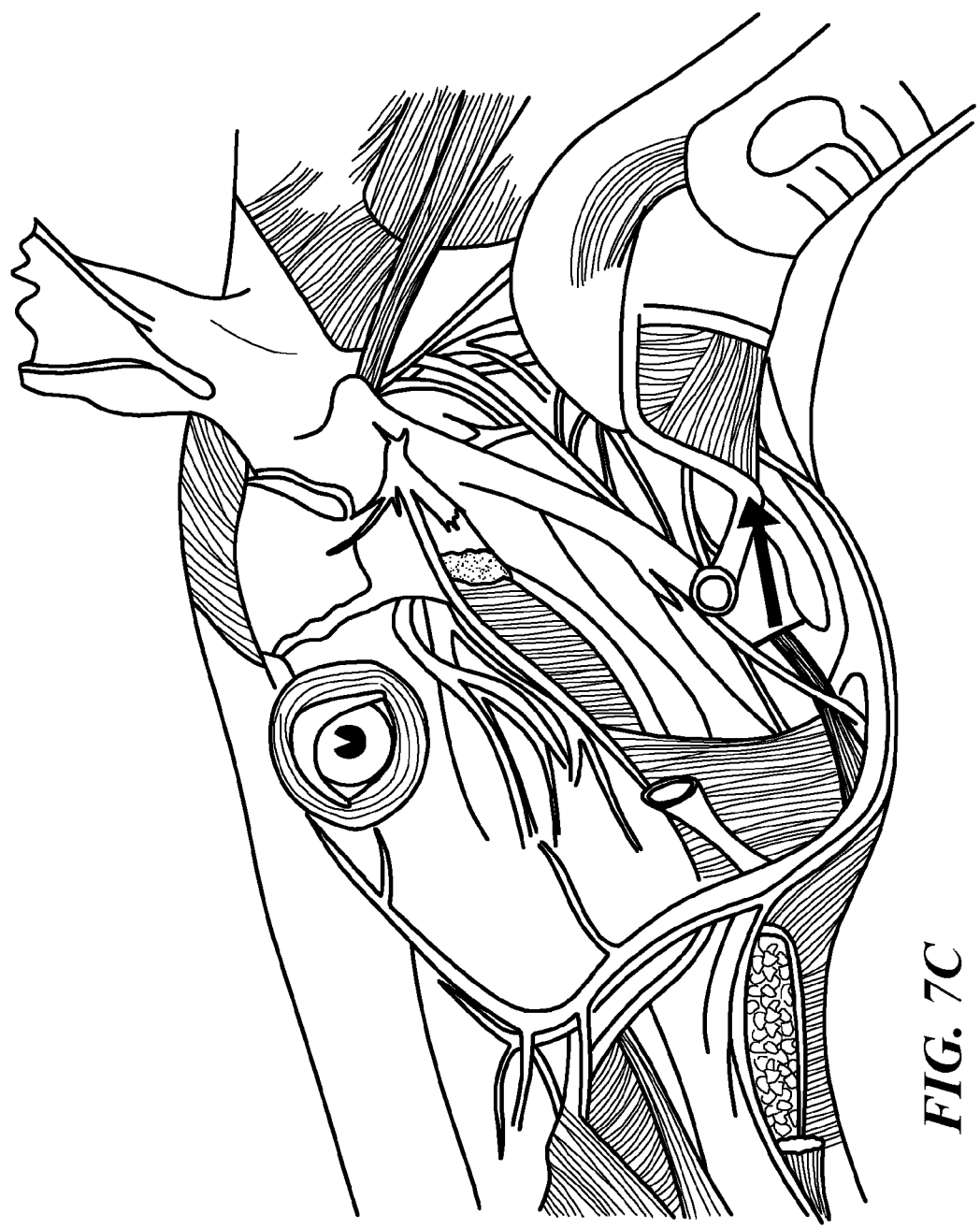
Figure 7D:
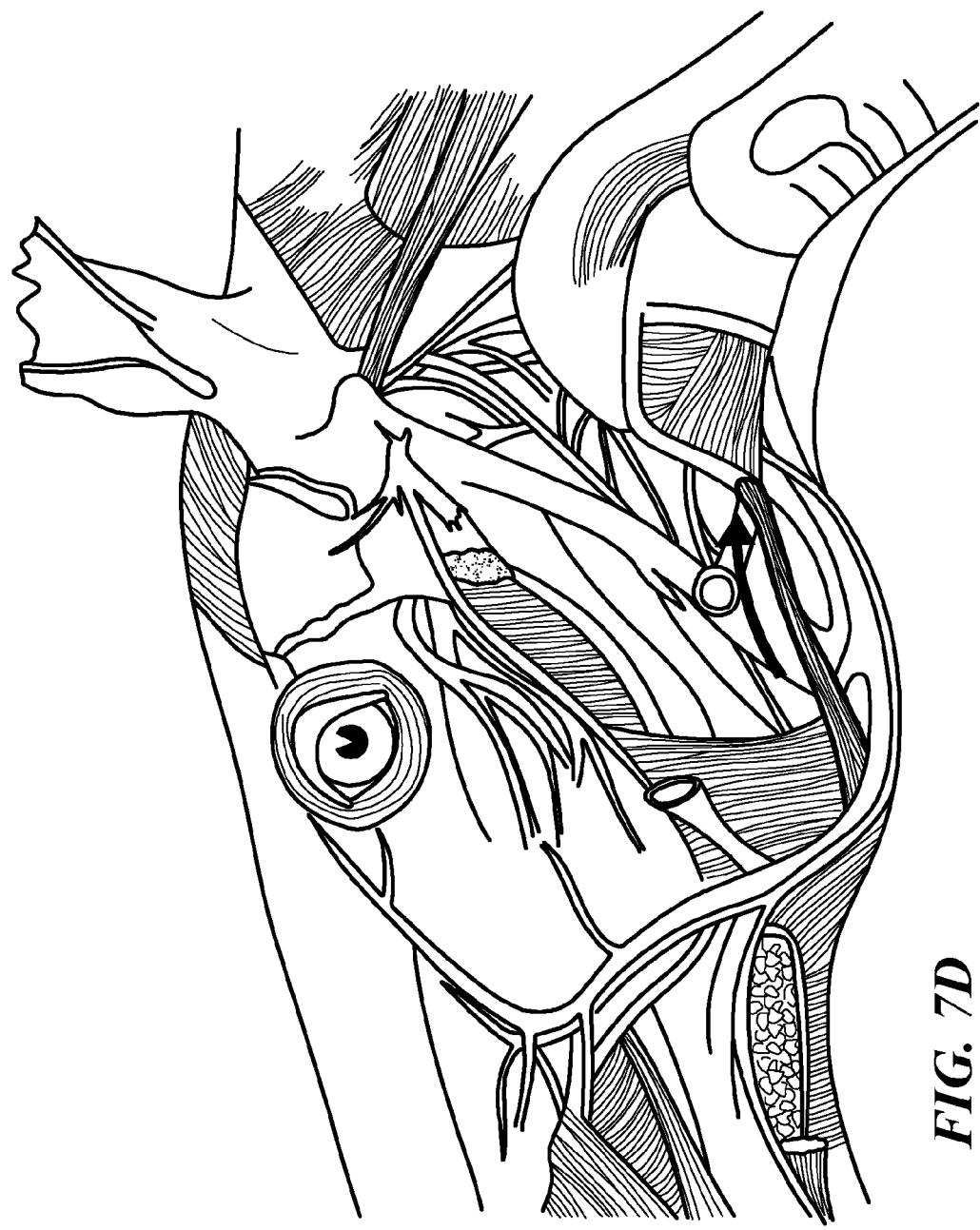
Figure 7E:
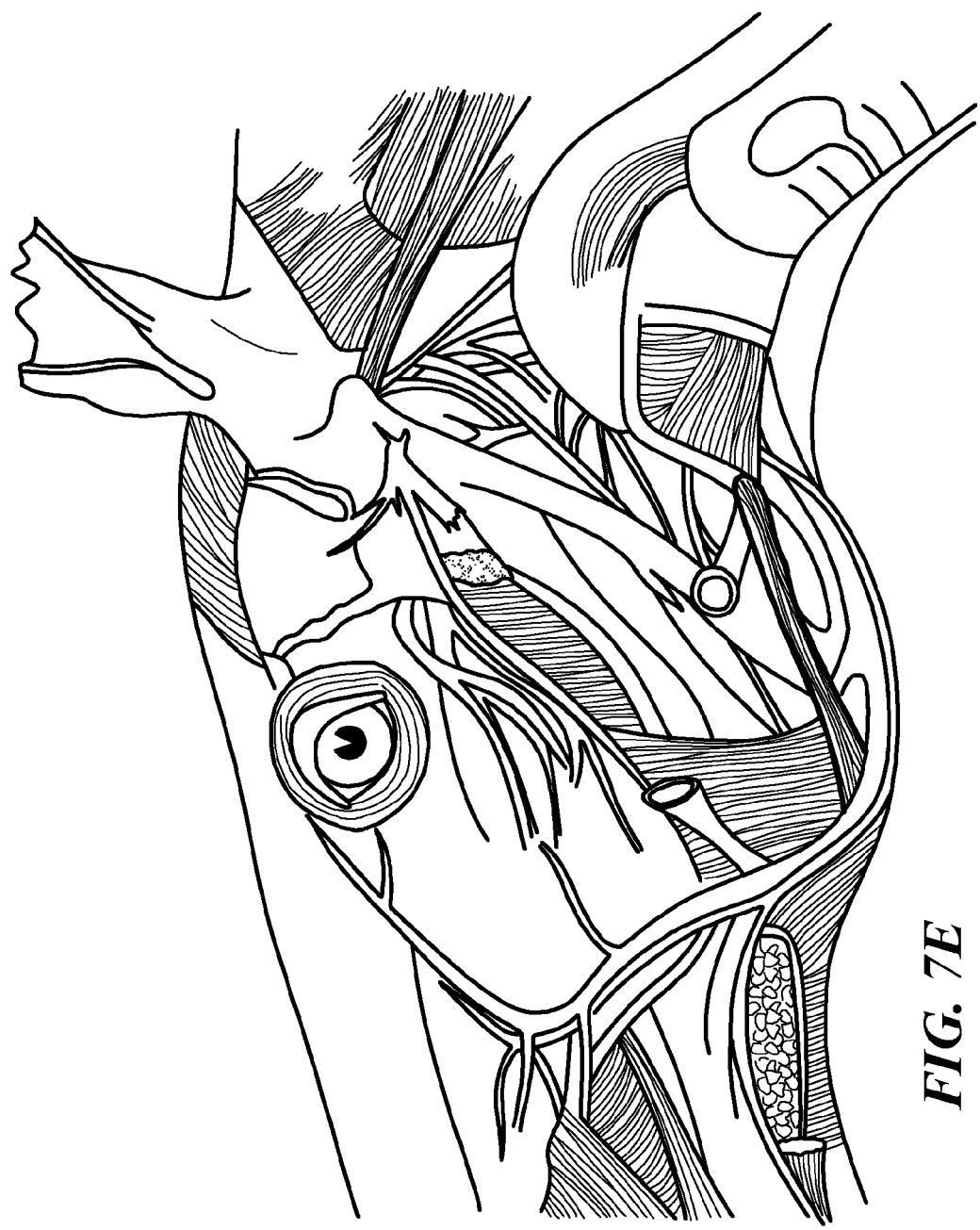

In step 113, the cut end is attached to the thyroid cartilage or thyrohyoid bone of the hyoid apparatus. FIG. 7C shows the movement direction of the cut end of the digastric muscle (arrow). FIGS. 7D and 7E show the cut end attached to the thyroid cartilage near the thyrohyoid bone attachment location.

Similar to process 100 above, in step 114, at least one stimulation parameter is generated with a processor. The stimulation system may include a processor 303, such as shown in FIGS. 5A and 5B, which may include a pulse generator that generates a stimulation parameter. The processor 303 may be implanted in the horse's chest or anywhere within the horse's neck area. In horses, the stimulation parameter may include biphasic waveforms, a phase duration of about 50 msec to 10,000 msec, in most subjects from about 250 msec to 1,000 msec, a magnitude per phase in the range of about 50 mA to 10,000 mA, in most subjects from about 250 mA to 1,000 mA, and a pulse rate of about 0.1 Hz to about 20,000 Hz, in most subjects from about 10 Hz to about 40 Hz. Appropriate stimulation systems that may be used with embodiments of the present invention are disclosed in U.S. Patent Publication No. 2008/0208280 by Lindenthaler incorporated by reference herein in its entirety.

In step 116, the trans-positioned digastric muscle is stimulated with the stimulation system in order to move the larynx position during the respiration process. The trans-positioned muscle may be stimulated either by a muscle electrode, by stimulating its/their innervating nerve(s), or by a reflex of the digastric muscle. For example, the stimulation system may include stimulating electrodes 301 that may be wrapped around or placed near or in contact with branches of the appropriate nerve(s). The stimulation system may include electrode leads 304 and optional safety loops 305, such as shown in FIG. 5B.

The stimulation of the trans-positioned muscle, or geniothyroid muscle, may be triggered by a variety of activities. For example, the stimulation may be triggered by the activity of the anterior belly (e.g., at the site of the chin) of the digastric muscle itself, the activity of the anterior belly of the digastric muscle after the patient has been trained to willingly contract it before swallowing, by the detection of an activity of another muscle involved in the swallowing process, by the detection of an activity of another muscle involved in the respiration process or by manually activating the stimulation by the patient or another person.

Figure 8:
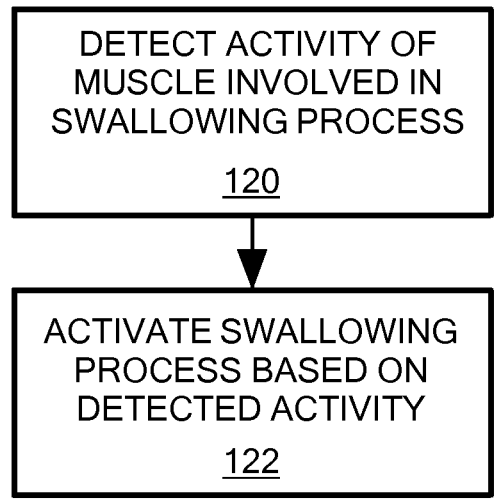
FIG. 8 is a flow chart illustrating a method for automatically activating the swallowing process in a subject using a detected activity in accordance with an embodiment of the invention.
Figure 8A:
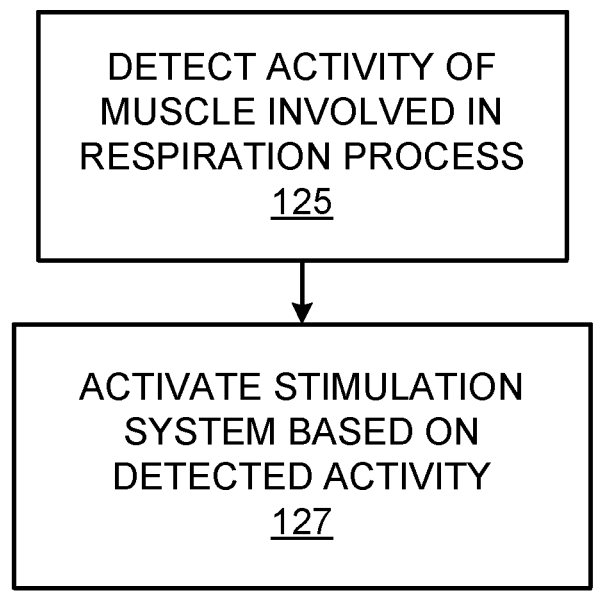
FIG. 8A is a flow chart illustrating a method for automatically activating a stimulation system in a horse based on a detected activity in accordance with an embodiment of the invention.

Thus, the stimulation system may include one or more sensing electrodes (not visible) to automatically detect the activity or a manual activator that may be activated by the patient or another person, e.g., a switch or toggle, instead of, or in addition to, the sensing electrodes. For example, FIG. 8 shows a process for automatically activating the swallowing process using a detected activity in a subject. The process begins at step 120 by detecting an activity of one or more muscles involved with the swallowing process. For example, the sensing electrode(s) may be configured to detect electromyographic (EMG) activity of a muscle involved in the swallowing process and/or to detect physical movement of one or more muscles related to the swallowing process. The sensing electrode may generate a first signal in response to the activity that has been detected. The first signal may be received at the processor 303, and the processor 303 may generate at least one stimulation parameter based on the first signal. The stimulation parameter from the processor 303 may be received by the one or more stimulating electrodes 301, and the stimulating electrode(s) 301 in turn stimulate the trans-positioned muscle (e.g., by stimulating the muscle, its/their innervating nerve(s), or a reflex of the anterior belly of the digastric muscle), based on the stimulation parameter in order to activate the swallowing process (step 122). FIG. 8A shows a process for automatically activating the stimulation system using a detected activity in a horse. The process begins at step 125 by detecting an activity of one or more muscles involved with the respiration process. For example, the sensing electrode(s) may be configured to detect electromyographic (EMG) activity of a muscle involved in the respiration process and/or to detect physical movement of one or more muscles related to the respiration process. The sensing electrode may generate a first signal in response to the activity that has been detected. The first signal may be received at the processor 303, and the processor 303 may generate at least one stimulation parameter based on the first signal. The stimulation parameter from the processor 303 may be received by the one or more stimulating electrodes 301, and the stimulating electrode(s) 301 in turn stimulate the trans-positioned muscle (e.g., by stimulating the muscle, its/their innervating nerve(s), or a reflex of the digastric muscle), based on the stimulation parameter in order to activate the stimulation system (step 127).

Figure 9:
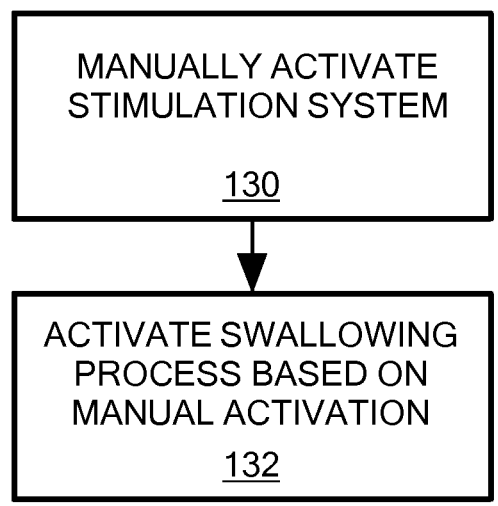
FIG. 9 is a flow chart illustrating a method for activating the swallowing process in a subject using a manual activation in accordance with an embodiment of the invention.
Figure 9A:
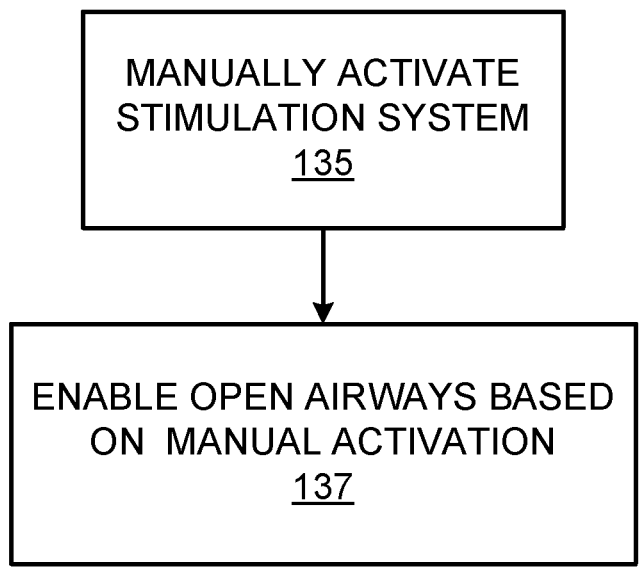
FIG. 9A is a flow chart illustrating a method for manually activating a stimulation system in a horse in order to ensure open airways in accordance with an embodiment of the invention.

Alternatively, FIG. 9 shows a process for manually activating the swallowing process. The process begins by manually activating the stimulation system in step 130. As mentioned above, the manual activator may be activated by the patient, such as a switch or toggle. The manual activator may send a first signal to the processor 303 in response to the manual activation, and the processor 303 may generate at least one stimulation parameter based on the first signal. As described above, the stimulation parameter from the processor 303 may be received by the one or more stimulating electrodes 301, and the stimulating electrode(s) 301 in turn stimulate the trans-positioned muscle based on the stimulation parameter in order to activate the swallowing process (step 132). FIG. 9A shows a process for manually enabling open airways in a horse. The process begins by manually activating the stimulation system in step 135. As mentioned above, the manual activator, such as a switch or toggle, may be activated by a person. The manual activator may send a first signal to the processor 303 in response to the manual activation, and the processor 303 may generate at least one stimulation parameter based on the first signal. As described above, the stimulation parameter from the processor 303 may be received by the one or more stimulating electrodes 301, and the stimulating electrode(s) 301 in turn stimulate the trans-positioned muscle based on the stimulation parameter in order to ensure open airways in the horse (step 137).

Alternatively, the stimulation may be untriggered, but the trans-positioned muscle may be hypertrophied. This means that the electrical stimulation may increase the muscle fiber cross-section of all activated fibers, thereby increasing muscle diameter and volume, which increases the resting tone of the muscle. The electrical stimulation may decrease the length of the resting and contracting muscle and muscle force, thereby narrowing/decreasing distance between chin and thyroid cartilage or thyrohyoid bone during resting and in particular during activation of the trans-positioned muscle. The electrical stimulation may increase the effects of narrowing/decreasing distance between the chin and the thyroid cartilage or thyrohyoid bone during activation of the trans-positioned muscle.

The stimulating electrodes and the sensing electrodes may be either bipolar or tripolar. Similarly, one electrode may be bipolar and one electrode may be tripolar. The electrode leads 304 should be sufficiently damage-resistant. The lead body should be arranged in a way, so that the nerve and the stimulator are influenced as little as possible by movements of the muscles, the neck, and the head.

Embodiments of the present system may be directed to a totally or partially implantable system in a human or -other animal, such as a horse. For example, the stimulator may include a housing that can be very small with all of the implant's electronic components contained in a robust and compact hermetically sealed case. Energy and necessary information may be inductively or optically transferred through the skin of the subject. This can be achieved by either enclosing the electronic circuitry inside a metallic case with a secondary coil placed aside or around the case. Similarly, this may be achieved by enclosing the electric circuitry and a secondary coil inside a dielectric case.

Some embodiments of the processor 303 may be implemented as hardware, software (e.g., a computer program product), firmware, or any combination of software, hardware, or firmware. For example, embodiments may be implemented as a computer program product for use with a computer system. Such implementation may include a series of computer instructions or program code fixed either on a tangible medium, such as a computer readable medium (e.g., a diskette, CD-ROM, ROM, or fixed disk) or transmittable to a computer system, via a modem or other interface device, such as a communications adapter connected to a network over a medium. The medium may be either a tangible medium (e.g., optical or analog communications lines) or a medium implemented with wireless techniques (e.g., microwave, infrared or other transmission techniques). The series of computer instructions may embody all or part of the functionality previously described herein with respect to the processor. Those skilled in the art should appreciate that such computer instructions may be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web).

While the invention has been described in connection with specific embodiments thereof, it will be understood that it is capable of further modification. This application is intended to cover any variation, uses, or adaptions of the invention and including such departures from the present disclosure as come within known or customary practice in the art to which the invention pertains.

What is claimed is:

1. A method of modifying larynx position in a horse, the method comprising:

cutting one end of digastric muscle;
attaching the cut end of the digastric muscle to thyroid cartilage or thyrohyoid bone, thereby trans-positioning the digastric muscle;
providing a stimulation electrode configured to stimulate the trans-positioned digastric muscle;
generating at least one stimulation parameter for the stimulation electrode using a processor; and
stimulating the trans-positioned digastric muscle with the stimulation electrode using the stimulation parameter in order to modify the larynx position.

2. The method according to claim 1, wherein the stimulating includes electrical stimulation of the digastric muscle, its innervating nerves, a reflex of the digastric muscle, or a combination thereof.

3. The method according to claim 1, further comprising:
providing a sensing electrode configured to detect activity of a muscle involved in respiration process and to generate a first signal based on the detected activity, wherein the at least one stimulation parameter is generated in response to receiving the first signal and the stimulation parameter is based on the first signal.

4. The method according to claim 3, wherein the sensing electrode is configured to detect electromyographic (EMG) activity of the muscle involved in the respiration process.

5. The method according to claim 3, wherein the sensing electrode is configured to detect physical movement activity of the muscle involved in the respiration process.

6. The method according to claim 1, wherein the stimulating is manually activated by a person.

7. The method according to claim 1, wherein the stimulating is activated by activity of the digastric muscle.

8. The method according to claim 1, wherein the stimulating modifies the larynx position by moving the larynx towards the chin.

* * * * *